United States Patent [19]

Maury

[11] 4,036,225
[45] July 19, 1977

[54] BICOMPARTMENTAL SYRINGE

[76] Inventor: Jean-Robert Maury, Le Peycher Montpeyroux de Lonchat (Dordogne), France

[21] Appl. No.: 614,363

[22] Filed: Sept. 18, 1975

[30] Foreign Application Priority Data

Sept. 19, 1974 France .................................. 74.31687

[51] Int. Cl.$^2$ .............................................. A61M 5/00
[52] U.S. Cl. ............................. 128/218 M; 128/272.1
[58] Field of Search .......... 128/218 M, 218 R, 218 D, 128/218 P, 272.1, 221, 220, 216

[56] References Cited

U.S. PATENT DOCUMENTS

| 2,591,706 | 4/1952 | Lockhart | 128/218 M |
| 2,655,919 | 10/1953 | Goodstein et al. | 128/218 M |
| 3,489,147 | 1/1970 | Shaw | 128/272.1 X |
| 3,511,239 | 5/1970 | Tuschoff | 128/218 M |
| 3,570,486 | 3/1971 | Engelsher et al. | 128/218 M |
| 3,724,460 | 4/1973 | Gomez et al. | 128/272.1 X |
| 3,785,379 | 1/1974 | Cohen | 128/218 M |
| 3,810,469 | 5/1974 | Hurschman | 128/218 M |

Primary Examiner—John D. Yasko
Attorney, Agent, or Firm—Wolf, Greenfield & Sacks

[57] ABSTRACT

The present invention relates a syringe for use in the distribution, conditioning and injection of two or more products to be mixed just before use, characteriZed in that it comprises two separate and contiguous compartments A and B, resulting from the assembly of two complimentary, joinable receptacles.

4 Claims, 1 Drawing Figure

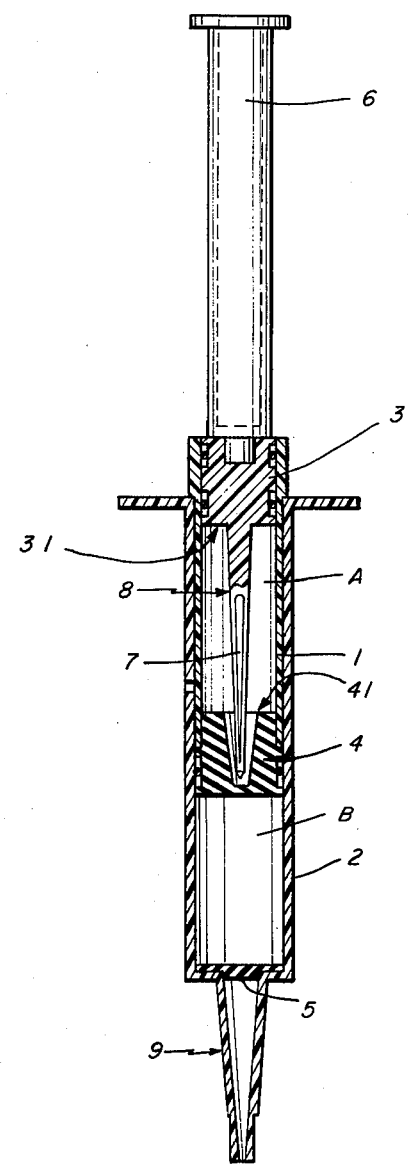

BICOMPARTMENTAL SYRINGE

The present invention relates to a bicompartmental syringe for use in the conditioning and injection of two products to be mixed just before use.

More specifically this syringe is for use in the pharmaceutical and medical fields for the distribution and conditioning, as well as for the administration to the organism of various therapeutically, prophylactically and diagnostically used substances.

In the present state of the art the various injectable, thereapeutic and prophylactic substances, such as medicaments, antibiotics, serums, vaccines, antigens, as well as reactive products for diagnostic use are generally distributed, conditioned and stored in sealed ampoules or in perforatable bottles.

Moreover, these substances are injected into the organism in general by means of a conventional syringe havng a monocompartmental syringe body and a piston. When it is desired to inject into the organism a medicament, such as for example penicillin which is usually commercially distributed in the form of powder in bottles, it is generally necessary to proceed in several stages.

In a first stage, the liquid solvent contained in a first receptacle such as a perforatable bottle or glass ampoule is taken up by means of a conventional syringe equipped with a terminal needle.

In a second state, the solvent liquid is injected by means of the same syringe into the receptable, perforatable bottle or glass ampoule containing the antibiotic substance in the pulverulent state.

In a third stage, after mixing and disolving the powder in the liquid solvent, in general the mixture is taken up and injected into the organism using the same syringe.

This procedure which involves the use of several receptacles and one syringe is performed in several stages in a microbiologically non-sterile atmosphere which can lead to a deterioration of the injected product. Moreover, the product may be spilled and lost if one of the receptacles is unfortunately overturned during these different operations. In the present state of the art the operations described hereinbefore necessitate several different containers and one syringe, having the disadvantage of being inconvenient, long, difficult and non-sterile.

The object of the present invention is to obviate the disadvantages described hereinbefore, and proposes the creation of a syringe having two separate compartments formed by assembling two complimentary members, each functioning as a receptacle and permitting the collection, distribution, conditioning, keeping and storage in an easy, practical, separate, sterile and hermetic manner of the various substances to be injected or administered to the organism.

To this end, the invention relates to a bicompartmental syringe, characterised in that it comprises a main body, sealed by means of a perforatable or selfbreakable terminal diaphragm and containing an inner member sealed at one end by a perforatable stopper, and at the other by a main piston equipped with a perforating needle to which is applied the syringe plunger, whereby the internal member forms the first compartment and is mounted within a portion of the main body and whereby the external member forms the second compartmentin the portion not occupied by the internal member, the products being mixed by operating the plunger which brings about the perforation of the stopper by the needle carried by the main piston, whereby the produce contained in the first compartment then flows via the perforating needle into the second compartment to form the mixture, injection taking place when the main piston is in contact with the stopper, the needle perforates the terminal diaphragm and the stopper actuated by the piston and the plunger introduces the liquid into the end fitting of the syringe carrying the hypodermic needle.

Thus, the syringe comprises both the conditioning receptacle for the two products to be mixed prior to use and the device for injecting the same. Moreover, by exerting pressure on the main pistion it is possible to bring about in a simple, convenient, automatic and sterile manner, the mixing of the various substances contained in the two compartments of the syringe body, as well as their progression and flow up to the end fitting of the syringe. , A device according to the invention is shown in nonlimitative manner in the drawing.

This drawing shows a schematic longitudinal section of the syringe according to the invention.

The main body of the syringe is formed by assembling two circular, complimentary and nestable hollow members made either of a transparent artificial plastic material (e.g. polyvinyl or polyethylene) or glass and represented by the internal member 1 and the external receptacle 2. These two members are assembled and the syringe body is formed in the following manner.

As inner terminal diaphragm 5, made from artificial plastic material (polyethylene) or perforatable rubber, is shaped on to the circular base of the external receptacle 2. The assembly formed by the diaphragm and the external receptacle represents the first portion of the syringe body and constitutes a cylindrical receptacle B which can receive and contain one or several pulverulent substances such as, for example, penicillins.

In its upper portion having the larger external diameter, the internal body 1 receives the main piston represented by member 3, made either from rubber or an artificial plastic material (e.g. nylon) and annular rubber cores and having on its front face a tapered 8 and grooved 7 extension made from metal or a hard artificial plastic material (e.g. nylon). The main body 1 and the main piston 3, assembled in this way, constitute a cylindrical receptacle A which can receive and contain one or several liquid substances such as physiological or antibiotic solvents in the liquid phase. After filling the above-mentioned receptacle receives a stopper 4 made from rubber or perforatable artificial plastic materials such as, for example, polyethylene.

Members 1, 3 and 4 together form the second part of the syringe body which is fitted into the external receptacle 2 to form the syringe, which is equipped with a plunger made from artificial plastic material (e.g. nylon or polyethylene), represented by member 6. The thus obtained assembly can be made irreversible, either by placing glue between members 1 and 2, or by the existence of a screw thread, not shown on the drawing, between members 1 and 2 of the syringe body.

The syringe obtained in this way can be placed and stored in a metal or plactic box until it is required for use.

During use, plunger 6 makes it possible to exert a pressure on the rear face of main piston 3, caused to move within the syringe body and which advances towards the end fitting. Therefore, the perforating needle 8, with which the piston is equipped perforates the internal intermediate diaphragm of stopper 4 and, due to its longitudinal semi-circular recess 7, drives the liquid in upper compartment A towards lower compartment B where it is mixed with the various pulverulent substances contained therein.

The main piston 3 is then supported by its front face 31 on the rear face 41 of member 4, which it moves before it into the syringe body. The needle 8 of the main piston reaches and then perforates the terminal diaphragm 5 and then due to its longitudinal recess 7 drives the mixture in solution in lower compartment B towards end fitting 9 of the syringe, and then towards the hypodermic needle.

According to another embodiment of the syringe, compartment A can contain, under a vacuum, one or several lyophilised substances, dried at low temperature. Moreover, compartment B contains one or several liquid substances serving as a solvent for the lyophilised substances. During the use of the syringe according to the invention the advance of the piston causes, as in the previous embodiment, the perforation of stopper 4. The vacuum in comartment A causes the sucking in of the liquid substances contained in compartment B and their passage via the longitudinal semi-circular recess 7 of tapered extension 8 into compartment A. After mixing and dissolving the substances in compartment A then undergo, under the pressure of the main piston, a return flow via the longitudinal recess of needle 8 to compartment B and then reach, as in the previous embodiment, end fitting 9 of the syringe after the perforation of the internal terminal diaphragm 5 by needle 8 of the main piston 3.

The syringe according to the invention can only be used once. The fundamental design of the device according to the invention only permits a single usage and involves the syringe being disposed of after use. in view of the legal regulations governing the use and re-use of syringes this feature forms a further improtant advantage of the syringe according to the invention.

The device according to the invention can be generally used in all cases where the separate conditioning and storage of several mixable substances are necessary up to the time of use. This device can also be used whenever the mixing of several mixable substances must be carried out simply, rapidly, conveniently and aseptically.

Therefore, the device according to the invention can be used in laboratories, the parmaceutical industry, human and veterinary medicine as well as having domestic applications.

Obviously the invention is not limited to the embodiment described and represented, and in fact numerous variants are possible thereto without passing beyond the scope of the invention.

I claim:

1. A combined mixing and injecting syringe comprising:
    a pair of complentary members joined to form an elongated compartment,
    piston means slideably disposed at one end of one of said members and having a needle-like extension extending therefrom toward the opposite end of the said one member,
    plunger means for moving said piston means toward said other membrs,
    a first diaphragm disposed in the elongated compartment intermediate the ends of the compartment and separating the compartment into two separate and isolated chambers which may each contain a different substance,
    and a second diaphragm disposed across said other member to define one end of the compartment,
    said needle-like extension of said piston means being positioned in one chamber before operation of said plunger means causes the extension to puncture said first diaphragm,
    and said extension having means defining an elongated recess extending along a substantial length of said extension toward the tip of the extension whereby communication of materials is permitted between chambers when the first diaphragm is punctured.

2. A syringe as set forth in claim 1 wherein said recess is exposed along the entire length thereof.

3. A syringe as set forth in claim 1 wherein the longitudinal recess of the extension has a semi-circular cross-section.

4. A syringe as set forth in claim 1 including means for telescopically joining the pair of members.

* * * * *